(12) United States Patent
Takahashi et al.

(10) Patent No.: US 6,215,517 B1
(45) Date of Patent: *Apr. 10, 2001

(54) ELECTRONIC ENDOSCOPE SYSTEM

(75) Inventors: Akihiro Takahashi, Tokyo; Kohei Iketani, Saitama-ken, both of (JP)

(73) Assignee: Asahi Kogaku Kogyo Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/057,603

(22) Filed: Apr. 9, 1998

(30) Foreign Application Priority Data

Apr. 14, 1997 (JP) .................................................... 9-111919
Apr. 14, 1997 (JP) .................................................... 9-111920

(51) Int. Cl.⁷ .................................................... H04N 7/18
(52) U.S. Cl. .................................................... 348/72; 348/65
(58) Field of Search .................................................... 348/65–66, 61, 348/71–72, 77, 45; 600/101, 109–113, 166, 172

(56) References Cited

U.S. PATENT DOCUMENTS

| | | | | |
|---|---|---|---|---|
| 4,816,909 | * | 3/1989 | Kimura et al. | 348/71 |
| 4,878,112 | * | 10/1989 | Ieoka | 348/70 |
| 4,891,695 | * | 1/1990 | Uchikubo et al. | 348/72 |
| 4,926,258 | * | 5/1990 | Sasaki et al. | 348/72 |
| 5,392,067 | * | 2/1995 | Konno et al. | 348/72 |
| 5,614,943 | * | 3/1997 | Nakamura et al. | 348/72 |
| 5,627,583 | * | 5/1997 | Nakamura et al. | 348/72 |
| 5,740,801 | * | 4/1998 | Branson | 128/653.1 |
| 5,877,819 | * | 3/1999 | Branson | 348/701 |
| 5,966,168 | * | 10/1999 | Miyazaki | 348/68 |

FOREIGN PATENT DOCUMENTS 9266883   10/1997   (JP) .................................................... H04N/7/18

OTHER PUBLICATIONS

"Outline of Multimedia Industrial Application", pp. 938–945, 1st Edition Printing dated Aug. 25, 1997.

* cited by examiner

*Primary Examiner*—Vu Le
(74) *Attorney, Agent, or Firm*—Greenblum & Bernstein, P.L.C.

(57) ABSTRACT

Disclosed is an electronic endoscope system which includes an endoscope unit having a solid-state imaging element which captures an image of an object and outputs an image signal, and a signal processing unit which receives the image signal from the imaging element and generates a plurality of digital video signals having different signal formats. The signal processing unit may have a plurality of signal output ports for outputting the plurality of digital video signals having different signal formats, respectively. Alternatively or optionally, the signal processing unit may have at least one signal selector which selects one of the plurality of digital video signals having different signal formats, and at least one output port through which the one of the plurality of digital video signal selected by the signal selector is output.

20 Claims, 8 Drawing Sheets

ELECTRONIC ENDOSCOPE SYSTEM

BACKGROUND OF THE INVENTION

The present invention relates to an electronic endoscope provided with an endoscope unit having a solid-state imaging element, and a signal processing unit for processing an image signal output by the solid-state imaging element.

An electronic endoscope system is generally provided with an endoscope unit which has a CCD (Charge Coupled Device) at a distal end of an insertion portion thereof for capturing image of an object to be observed. The electronic endoscope system is further provided with an image signal processing unit which processes an image signal output by the CCD to generate a video signal. The video signal is transmitted to a displaying device such as a CRT (Cathode Ray Tube) display or the like, and/or to auxiliary devices (peripheral devices). Conventionally, electronic endoscope systems output analog video signals such as an analog RGB signal, analog composite signal, analog S-video signal and the like.

Recently, the peripheral devices (including displaying devices) provided with digital video signal input terminals have become developed and used. Using such devices is advantageous since the digital video signal has less deterioration due to attenuation of transmitted signal and is free from noise.

Image formed by the video signal output by the electronic endoscope system may be observed not only by an operator of the endoscope but also by an assistance, and/or many other people. For example, the image may be displayed on a displaying device located at a place or room remote from the electronic endoscope system. For this purpose, there has been desired that the peripheral devices utilizing digital video signal, which is not easily deteriorated.

It may be possible to convert the analog video signal once output by the conventional electronic endoscope into the digital video signal using an Analog to Digital (A/D) converter, and transmit the same to a peripheral device using the digital video signal. In such a method, however, the analog signal is once output, and then it is converted into the digital signal. Therefore, deterioration of the signal is unavoidable.

Further, a converting device for converting the analog signal to the digital signal should be additionally used together with the conventional electronic endoscope system, the number of cables for transmitting signals increased. Furthermore, the configuration of the endoscope system, operation thereof are complicated since the number of devices to be operated increases. Still further, a room for accommodating such a converting device should also become necessary. Therefore, using the A/D conversion together with the conventional electronic endoscope outputting the analog image signals is not practical.

Further to the above, various formats of digital video signals have been known. If there are plurality of peripheral devices which use digital video signals having different formats, a plurality of converting devices respectively corresponding to the formats of the video signals used by the plurality of peripheral devices should be employed in the electronic endoscope system.

SUMMARY OF THE INVENTION

It is therefore an object of the invention to provided an improved electronic endoscope system in which a video signal can be transmitted to a plurality of peripheral devices without deteriorating the video signal.

For the object, according to the invention, there is provided an electronic endoscope system which includes an endoscope unit having a solid-state imaging element which captures an image of an object and outputs an image signal, and signal processing unit, which receives the image signal from the imaging element and generates a plurality of digital video signals having different signal formats.

Since a plurality of digital video signals having different formats are generated, various types of peripheral devices utilizing digital video signals can be connected to the endoscope system, and the video signal can be transmitted without being deteriorated.

Optionally, the signal processing unit may be provided with a plurality of signal output ports for outputting the plurality of digital video signals having different signal formats, respectively.

With this configuration, a plurality of digital video signals having different formats can be output simultaneously. Accordingly, various types of peripheral devices using different signal formats can be connected to the endoscope system simultaneously.

Further optionally, the plurality of signal output ports may include at least one serial port for outputting one of the plurality of digital video signals.

Alternatively or optionally, the plurality of signal output ports may include at least one parallel port for outputting at least one of the plurality of digital video signals.

Still optionally or alternatively, the plurality of signal output ports may include at least one pair of serial and parallel ports for outputting at least one of the plurality of digital video signals having different signal formats as serial and parallel digital signals, respectively.

In particular case, the plurality of signal output ports may include a plurality of pairs of serial and parallel ports for outputting all of the plurality of digital video signals having different signal formats as serial and parallel digital signals, respectively. In this case, it is preferable that each pair of a parallel port and a serial port corresponding to the same signal format are arranged closely adjacent to each other to enable an operator to recognize a port to be used easily.

Alternatively, the signal processing unit may be provided with at least one signal selector, which selects one of the plurality of digital video signals having different signal formats; and at least one output port through which the one of the plurality of digital video signal selected by the signal selector is output.

Optionally, at least one output port may include a serial port for outputting a serial digital signal.

Alternatively or optionally, at least one output port may include a parallel port for outputting a parallel digital signal.

In particular case, the signal processing unit may include a first signal selector, which selects a first signal from among the plurality of digital video signals having different signal formats; a second signal selector, which selects a second signal from among the plurality of digital video signals having different signal formats; a parallel output port through which the first signal is output as a parallel digital signal; and a serial output port through which the second signal is output as a serial digital signal.

Preferably, the plurality of digital video signal may include a signal having a D1 format.

Alternatively or optionally, the plurality of digital video signal may include a signal having a D2 format.

Optionally, the plurality of digital video signal may include a digital brightness signal.

Further optionally, the plurality of digital video signal may include digital color difference signals.

Still optionally, the plurality of digital video signal may include a multiplexed signal which is generated by multiplexing color difference signals.

Yet optionally, the plurality of digital video signal may include a multiplexed signal which is generated by multiplexing brightness and color difference signals.

Furthermore, it is preferable that the signal processing device may output a field indication signal indicating whether a currently output signal corresponds to an odd or even frame.

Further optionally, the signal processing device may output a plurality of analog video signals.

BRIEF DESCRIPTION OF THE ACCOMPANYING DRAWINGS

DESCRIPTION OF THE EMBODIMENTS

Figure 1:
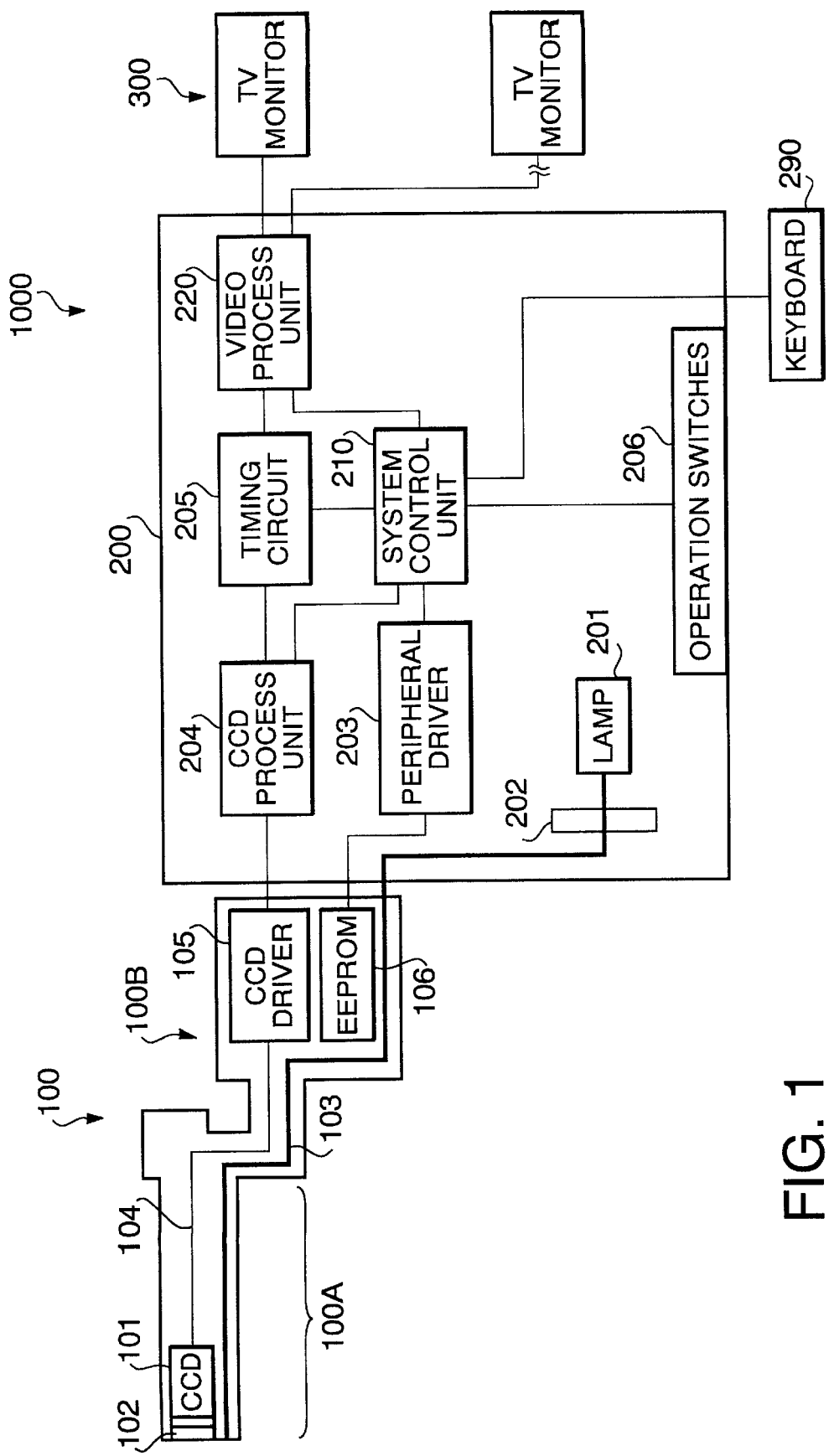
FIG. 1 shows a block diagram schematically illustrating a system configuration of an electronic endoscope system to which the present invention is applied.

FIG. 1 is a block diagram illustrating a schematic system configuration of an electronic endoscope system 1000 to which the present invention is applied.

The electronic endoscope 1000 includes an electronic endoscope unit 100, a light source unit 200, and a monitor unit 300.

The endoscope unit 100 has an insertion portion 100A which is formed of a flexible tube. At a distal end of the insertion portion 100A, a CCD (Charge Coupled Device) image sensor 101 (which will be referred to as the CCD, hereinafter), and an objective lens system 102 in front of (i.e., on an object side of) the CCD 101. An optical image of the object to be observed is formed by the objective lens system 102 on a light receiving surface of the CCD 101.

The endoscope unit 100 encloses a light guide 103 made of a bundle of optical fibers. One end of the light guide 103 is located at the distal end of the insertion portion 100A. Light is incident from the other end of the light guide 103, and is emerged toward the object from the distal end side thereof.

The electronic endoscope 100 is coupled to the light source unit 200 by means of a connection unit 100B. In the connection unit 100B, a CCD driver 105 for driving the CCD 101 is provided. The CCD driver 105 is connected with the CCD 101 through a cable 104. Driven by the CCD driver 105, the CCD 101 accumulates electronic charge in accordance with the optical image formed by the objective lens system 102, and outputs the image signal which is transmitted to the CCD driver 105.

The electronic endoscope system 1000 obtains a color image signal corresponding to each of 3 primary colors (R: Red; G: Green; and B: Blue) with use of a surface sequential method. Specifically, the object is illuminated by red light, green light and blue light, respectively, then image signal for each color component is obtained on a frame basis and stored in a memory. Various video signals are generated based on thus obtained image signals.

One end (i.e., a light emerging end) of the light guide 103 is fixedly secured at the distal end of the insertion portion 100A. The light guide 103 extends past through the insertion portion 100A, the connection unit 100B, and the other end (i.e., a light incident end) of the light guide 103 is fixed in the connection unit 100B, at a position where the light incident end side surface faces a lamp 201 of the light source unit 200.

In order to obtain the image signal for each color component on a frame basis with use of the surface sequential method, the object to be observed is illuminated with the red light, green light and blue light sequentially, and the optical image is formed on the CCD 101 by the objective lens system 102.

In order to illuminate the object with the red, green and blue light, an RGB rotatable filter 202 is provided between an light incident end side of the light guide 103 and the lamp 201. The light emitted by the lamp 201 is a so-called white light which includes all the red, green and blue light components. Light emitted by the lamp 201 is converged on the light incident end side of the light guide 103 through the RGB rotatable filter 202.

The RGB rotatable filter 202 is a disk-shaped filter on which a red (R) filter, a green (G) filter, a blue (B) filter and a light shielding portion are alternately formed. When the RGB rotatable filter 202 is rotated by a motor (not shown), the R filter, G filter, B filter are alternately inserted in an optical path from the lam 201 to the light guide 103 at a predetermined period. Accordingly, the red, green and blue light is intermittently projected to the object at the predetermined period.

In the connection unit 100B, an EEPROM (Electronically Erasable Programmable Read Only Memory) 106 is accommodated. The EEPROM stores data representing a type of the endoscope unit 100, data related to characteristics of the CCD 101 and the like. The data stored in the EEPROM 106 is retrieved by a peripheral driver 203, and then transmitted to a system control unit 210 which controls operation of the electronic endoscope system 1000.

To the system control unit 210, a CCD process unit 204 which controls operation of the CCD driver 105 is connected. Further, the CCD process unit 204 receives the image data output by the CCD 102 through the CCD drive 105. As described above, the electronic endoscope system 1000 employs the surface sequential method, and the image signals corresponding to the RGB color components are transmitted on a frame basis. The CCD process unit 204 applies analog-to-digital conversion to each of the image signals corresponding to the RGB color components, and stores the converted signal as image data in RGB frame memories 221, 222, 223 provided in a video process unit 220.

Driving of the CCD 101, rotation of the RGB rotatable filter 202, A/D conversion of the CCD process unit 204, storing image data in the frame memories 221, 222 and 223, are carried out synchronously with a clock signal generated by a timing circuit 205.

The image signal processing device 200 is provided with panel switches 206 on a body of the image signal processing device 200 for carrying out various operations. Operation status of the panel switches 206 are input in the system control unit 210. The system control unit 210 is further connected with a keyboard 290, through which various operation commands and/or data can be input to the system control unit 210. The video process unit 220 generates and outputs video signal in accordance with the image data of each of RGB components.

Figure 2:
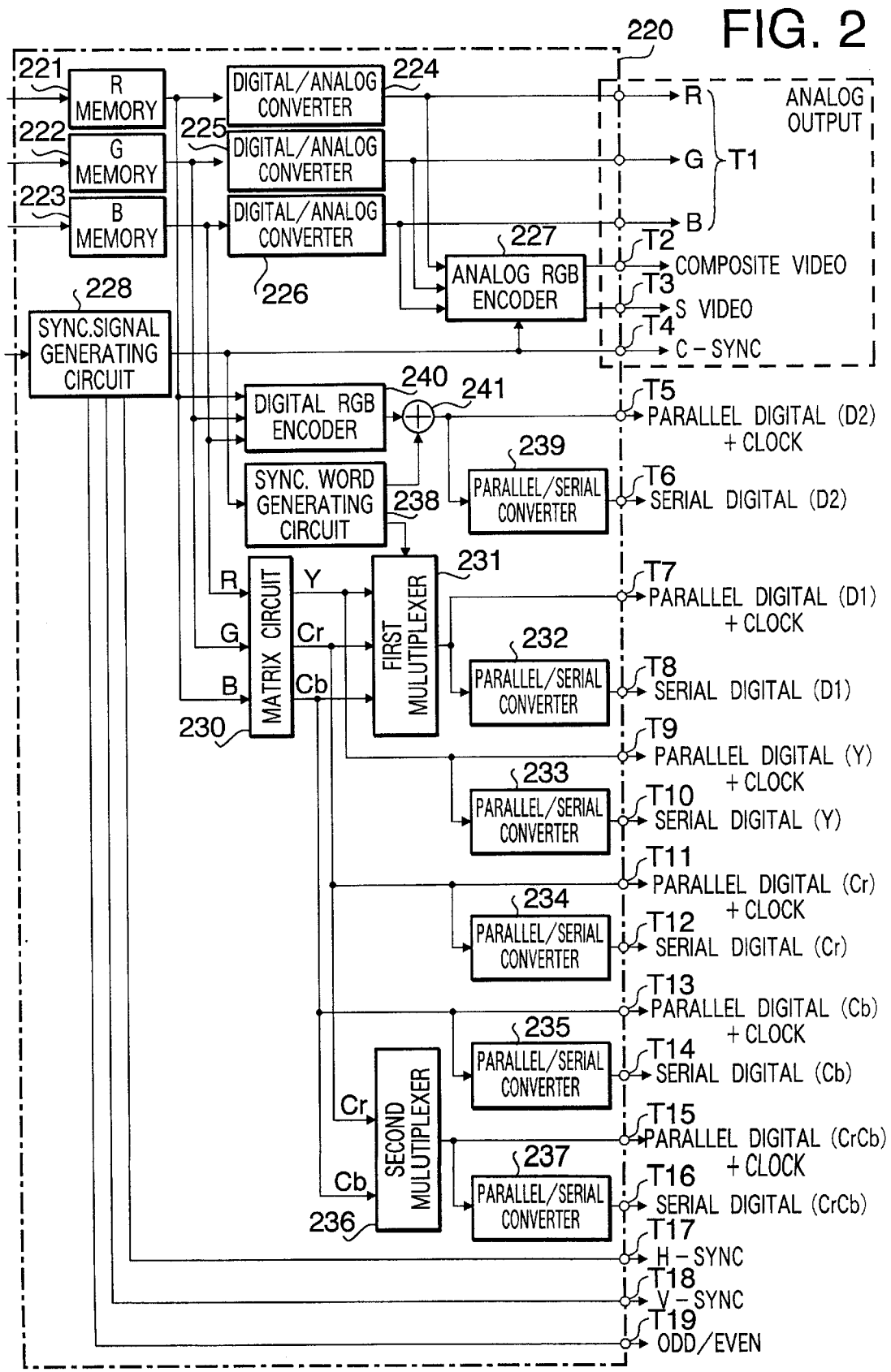
FIG. 2 shows an exemplary signal format of a digital video signal.

FIG. 2 is a block diagram of a video process unit 220 according to a first embodiment of the invention.

As described above, the video process unit 220 includes the RGB frame memories 221, 222 and 223. Data stored in the RGB frame memories 221, 222 and 223 is respectively transmitted to D/A (digital to analog) converters 224, 225 and 226, which output analog RGB signals through output ports T1 as shown in FIG. 2.

The analog RGB signals output by the D/A converters 224, 225 and 226 are also transmitted to an analog RGB encoder 227. The analog RGB encoder 227 generates a brightness signal and color difference signals, and further, based on the brightness signal and color difference signals, generates a composite video signal (analog) and an S video signal, which are output through output ports T2 and T3, respectively.

The video process unit 220 also has a synchronizing signal generating circuit 228, which generates a composite synchronizing signal C-SYNC by combining a horizontal synchronizing signal H-SYNC and a vertical synchronizing signal V-SYNC, and outputs the same through a port T4. The horizontal synchronizing signal H-SYNC and the vertical synchronizing signal V-SYNC are also output through ports T17 and T18, respectively. Further, the synchronizing signal generating circuit 228 outputs a frame signal ODD/EVEN indicating whether the data output from the RGB frame memories 221, 222 and 223 corresponds to an odd frame or an even frame through a port T19.

It should be noted that the above-described analog RGB signals, the composite video signal and the S video signal are analog video signals and conventional electronic endoscope system can also output the similar signals.

Next, digital video signals output by the electronic endoscope in various formats will be described.

The video process unit 220 includes a matrix circuit 230. The matrix circuit 230 receives the RGB digital signals transmitted from the RGB frame memories 221, 222 and 223, and converts the same into component signals, i.e., a brightness signal Y, a color difference signal Cr (i.e., R-Y) and a color difference signal Cb (i.e., B-Y) in D1 format such that ratio of sampling frequencies therefor is 4:2:2. Specifically, the sampling frequency for the brightness luminance signal Y is 13.5 MHz, and the sampling frequencies for the color difference signals Cr and Cb are both 6.75 MHz. A clock frequency used is twice the sampling frequency for the brightness signal Y, i.e., 27 MHz.

If sampled under the above condition, the number of samplings within an effective image period of one scanning line is 720 for the brightness signal Y, and 360 for each of the color difference signals Cr and Cb. Thus, the total number of the samplings is 1440.

Figure 3:
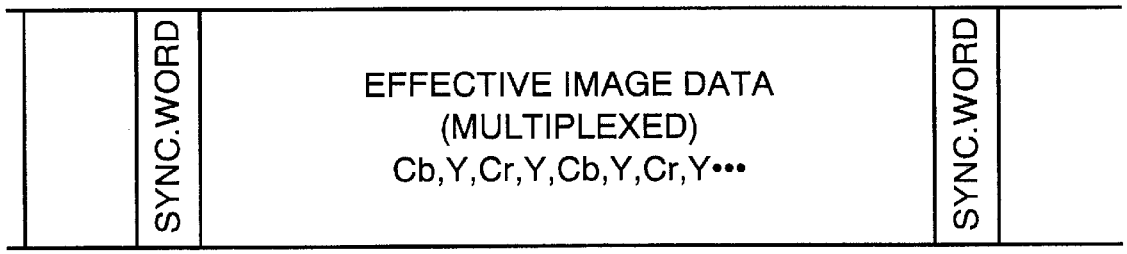
FIG. 3 is a chart illustrating a parallel-to-serial conversion.
Figure 4:
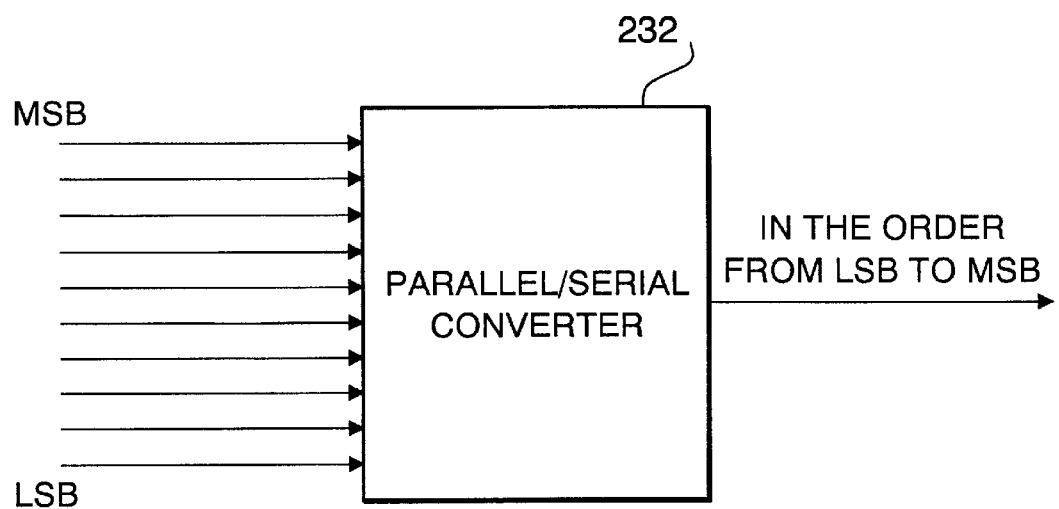
FIG. 4 is a block diagram of a video process unit according to a first embodiment of the invention.

The converted brightness signal Y and the color difference signals Cr and Cb are multiplexed by a first multiplexer 231 in the order of Cb, Y, Cr, Y, Cb, Y . . . , and further a synchronizing word generated by a synchronizing word generating circuit 238 is added before and after the multiplexed signals for one line. The structure of thus generated signal is schematically shown in FIG. 3. The signal shown in FIG. 3 is output through port T7 as a parallel digital video signal in D1 format. It should be noted that the output port T7 is a port for outputting a parallel digital video signal, and therefore includes a plurality of output terminals. To avoid a complicated drawing, the port T7 is represented by a single circle in FIG. 2. As for the other ports outputting the parallel digital signals, similar to the port T7, a plurality of terminals will not be shown in the drawings or described.

The signal output by the first multiplexer 231 is transmitted to a parallel/serial converter 232. The parallel/serial converter 232 converts the parallel digital video signal output by the first multiplexer 231 into a serial digital signal starting from an LSB (Least Significant Bit) of the parallel digital video signal at a transmission rate of 270 Mb/sec which is ten times the clock frequency of 27 MHz, and output the same through a port T8.

The brightness signal Y, the color difference signals Cr and Cb output by the matrix circuit 230 are also output through ports T9, T11 and T13, respectively, together with the clock signal. Similar to the port T7, the ports T9, T11, T13 also have a plurality of output terminals.

Further, the brightness signal Y, the color difference signals Cr and Cb output by the matrix circuit 230 are transmitted to parallel/serial converters 233, 234 and 235, converted into serial digital signals, and output through ports T10, T12 and T14, respectively, at a transmission-rate of 270 Mb/sec. The parallel digital signals output through the ports T9, T11, and T13 correspond to the serial digital signals output through the ports T10, T12 and T14, respectively.

The video process unit 220 is further provided with a second multiplexer 236 which receives the color difference signals Cr and Cb from the matrix circuit 230, multiplexes the same, and outputs the multiplexed color difference signal (CrCb) together with the clock signal as a parallel digital signal through a port T15. The output signal of the second multiplexer 236 is also transmitted in a parallel/serial converter 237 which converts the parallel digital signal output by the second multiplexer 236 into a serial signal corresponding thereto and having a transmission rate of 270 Mb/sec. The serial digital signal (i.e., the multiplexed color difference signals) converted by the parallel/serial converter 237 is output through a port T16.

The digital signals output by the RGB frame memories 221, 222 and 223 are also transmitted to a digital RGB encoder 240, which generates a digital composite signal based on the RGB image signals transmitted from the RGB frame memories 221, 222 and 223. A sampling frequency of the digital RGB encoder 240 for the composite signal is 4 times the frequency of a sub-carrier: 14.3 MHz for the NTSC system; and 17.7 MHz for the PAL system.

To the digital composite video signal output by the digital RGB encoder 240, an output signal of the synchronizing word generating circuit 238 is added by an adder 241, and supplied to a peripheral device through a port T5 as the digital composite video signal in D2 format.

A parallel/serial converter 239 converts the parallel signal output by the adder 241 into a serial signal which is transmitted through a port T6 at a transmission rate of 143 Mb/sec for NTSC system, or 177 Mb/sec for PAL system, from the LSB to MSB.

As described above, the video process unit 220 is provided with a plurality of ports through which various types of analog and digital video signals can be output. Accordingly, when a peripheral device such as a TV monitor 300, a printer, or the like is to be connected to the electronic endoscope system 1000, appropriate ports can be used in accordance with the format used in the peripheral device to be connected.

In the above embodiment, each of the D1 format signal, the D2 format signal, the Y signal, the Cr signal, the Cb signal, the multiplexed Cr and Cb signal is output as either the parallel or serial digital signal. The format of the digital signal is not limited to the described ones, but various formats can be used.

Further, each of the digital signals is not necessarily be output as either the parallel or serial digital signal. For example, it may be modified such that the D1 format signal is output as a parallel signal, and the D2 format signal is output only as a serial signal.

Furthermore, generation of output signals needs not be limited to the above-described method.

Figure 9:
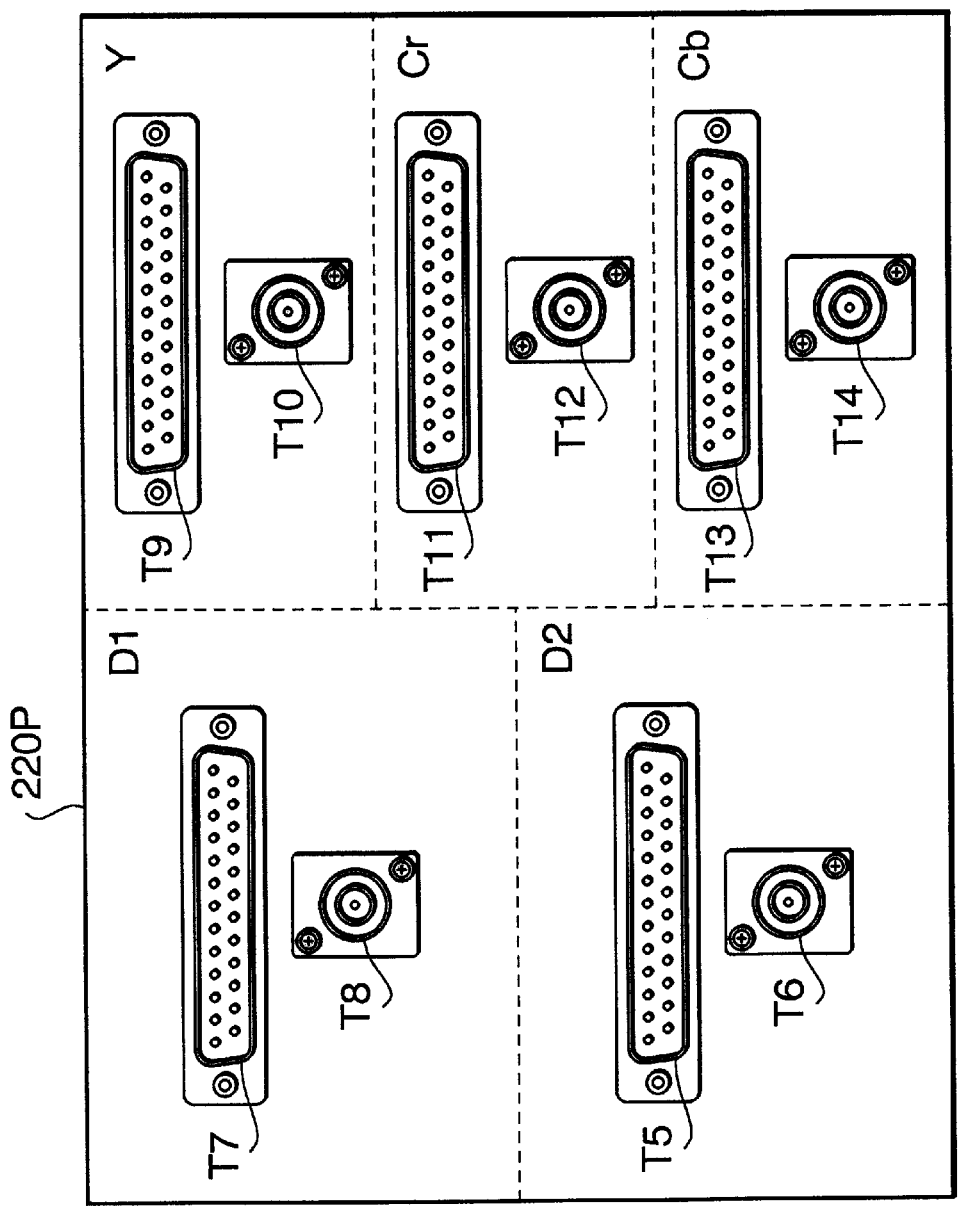
FIG. 9 shows an example of an arrangement of serial and parallel output ports of the video process unit according to the first embodiment of the invention.

For practical use, it is preferable that the serial and parallel ports corresponding to the same digital signal are arranged adjacently to each other. An example of an arrangement of the serial and parallel ports T5 through T14 provided on a portion 220P of the video processing unit 220 is shown in FIG. 9. In this example, for the serial ports T6, T8, T10, T12 and T14, a BNC type connector is used; and for the parallel ports T5, T7, T9, T11 and T13, a D-sub connector is used. As shown in FIG. 9, the portion 220P is divided into a plurality of areas corresponding to respective digital signals described above, and in each area, a pair of the serial and parallel ports (i.e., connectors) are provided. With this arrangement, an operator recognizes a port to be used easily, and accordingly, erroneous connection may be prevented.

Hereinafter, modification of the first embodiment will be described as second through seventh embodiments. In the following description and corresponding drawings, the same reference numerals are assigned to the elements employed in the first embodiment, and description thereof will be omitted.

Figure 5:
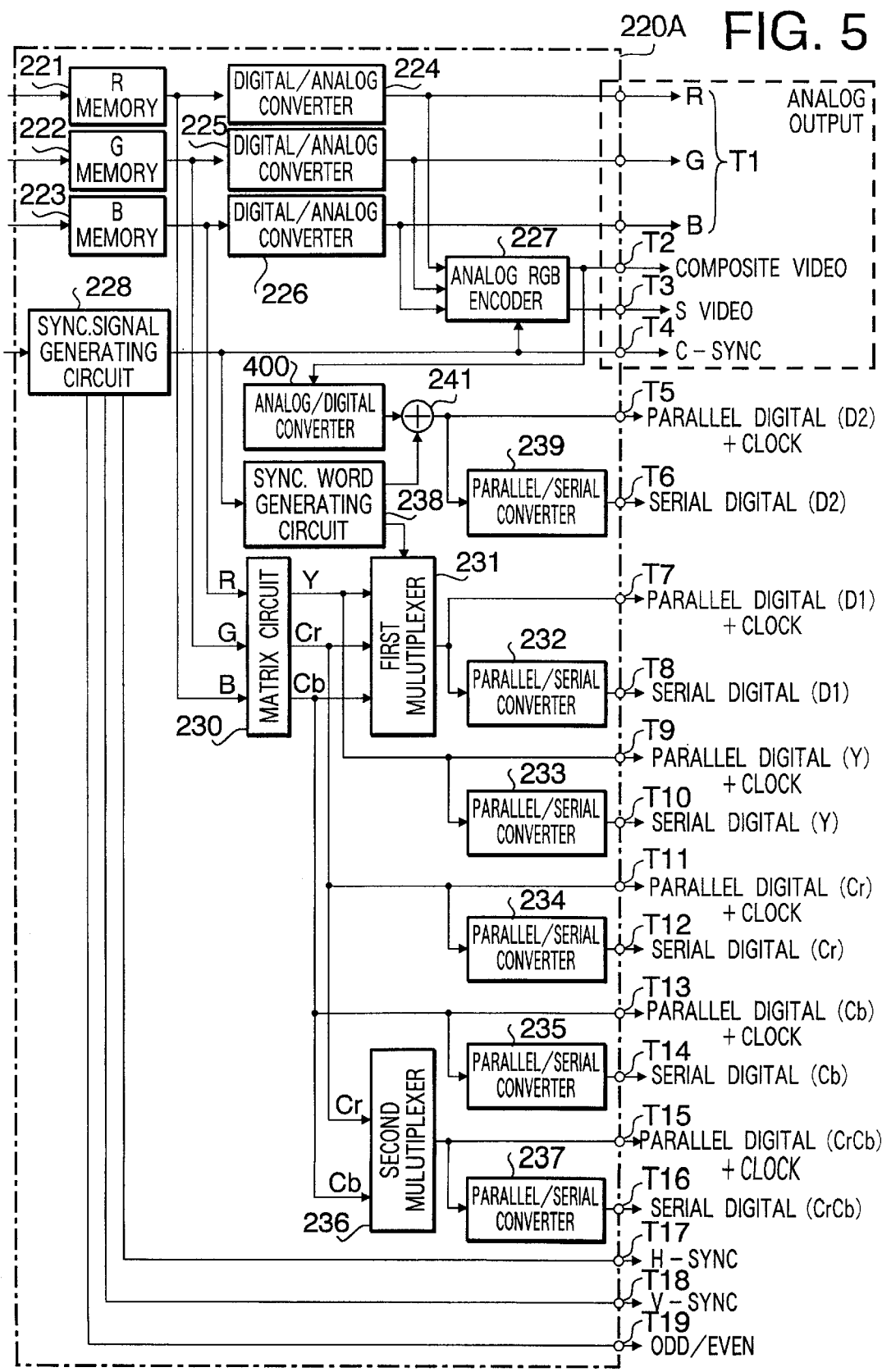
FIG. 5 is a block diagram of a video process unit according to a second embodiment of the invention.

FIG. 5 shows a video process unit 220A according to a second embodiment which is a modification of the above-described embodiment. In the second embodiment, the D2 format signal may be generated by converting the output signal of the analog RGB encoder 227 by means of an A/D converter 400.

Figure 6:
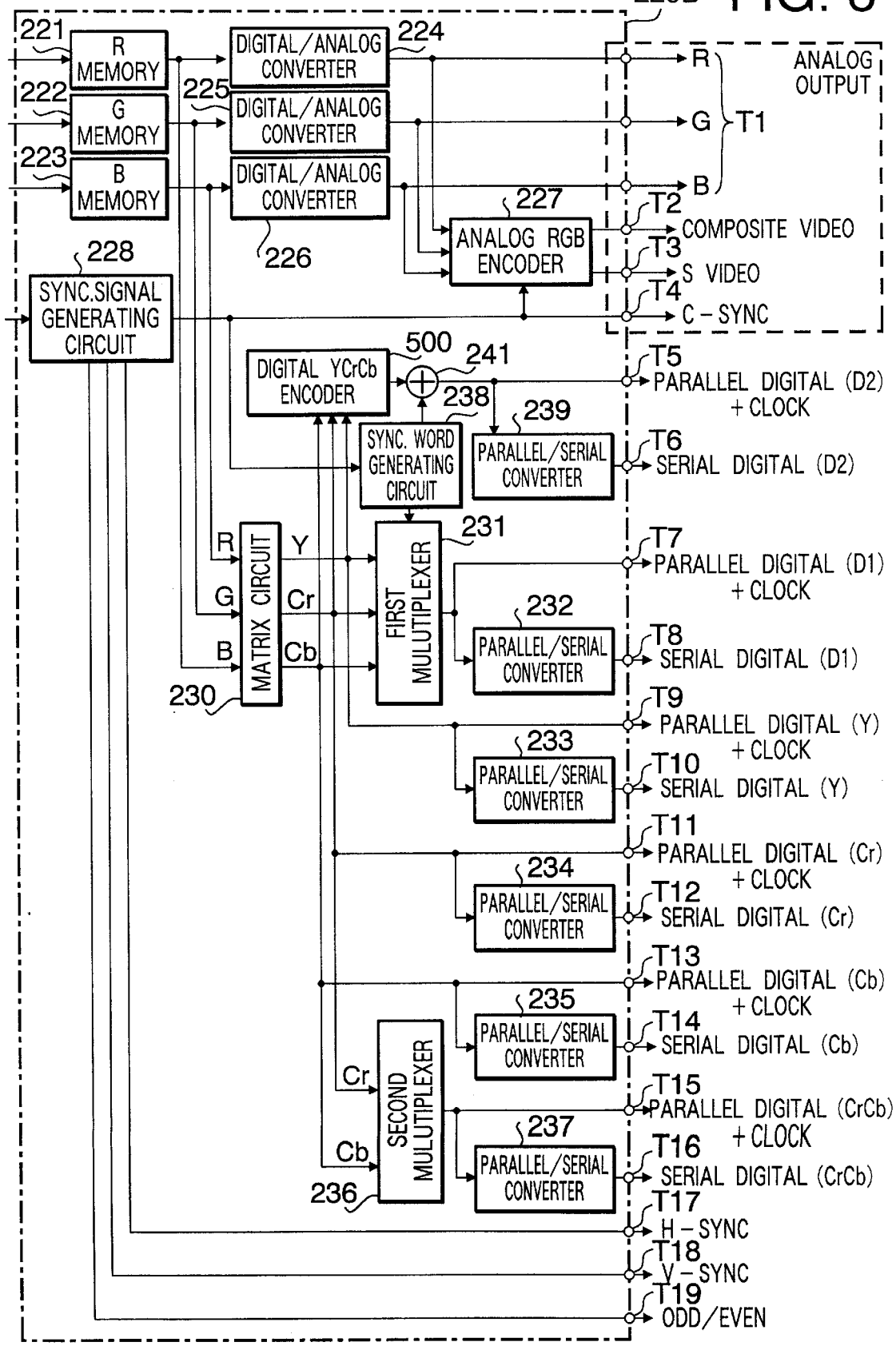
FIG. 6 is a block diagram of a video process unit according to a third embodiment of the invention.

FIG. 6 shows a video process unit 220B according to a third embodiment which is also a modification of the first embodiment. In the third embodiment, the D2 format signal is generated by a digital YCrCb encoder 500 using the brightness signal Y and color difference signals Cr and Cb output by the matrix circuit 230.

Figure 7:
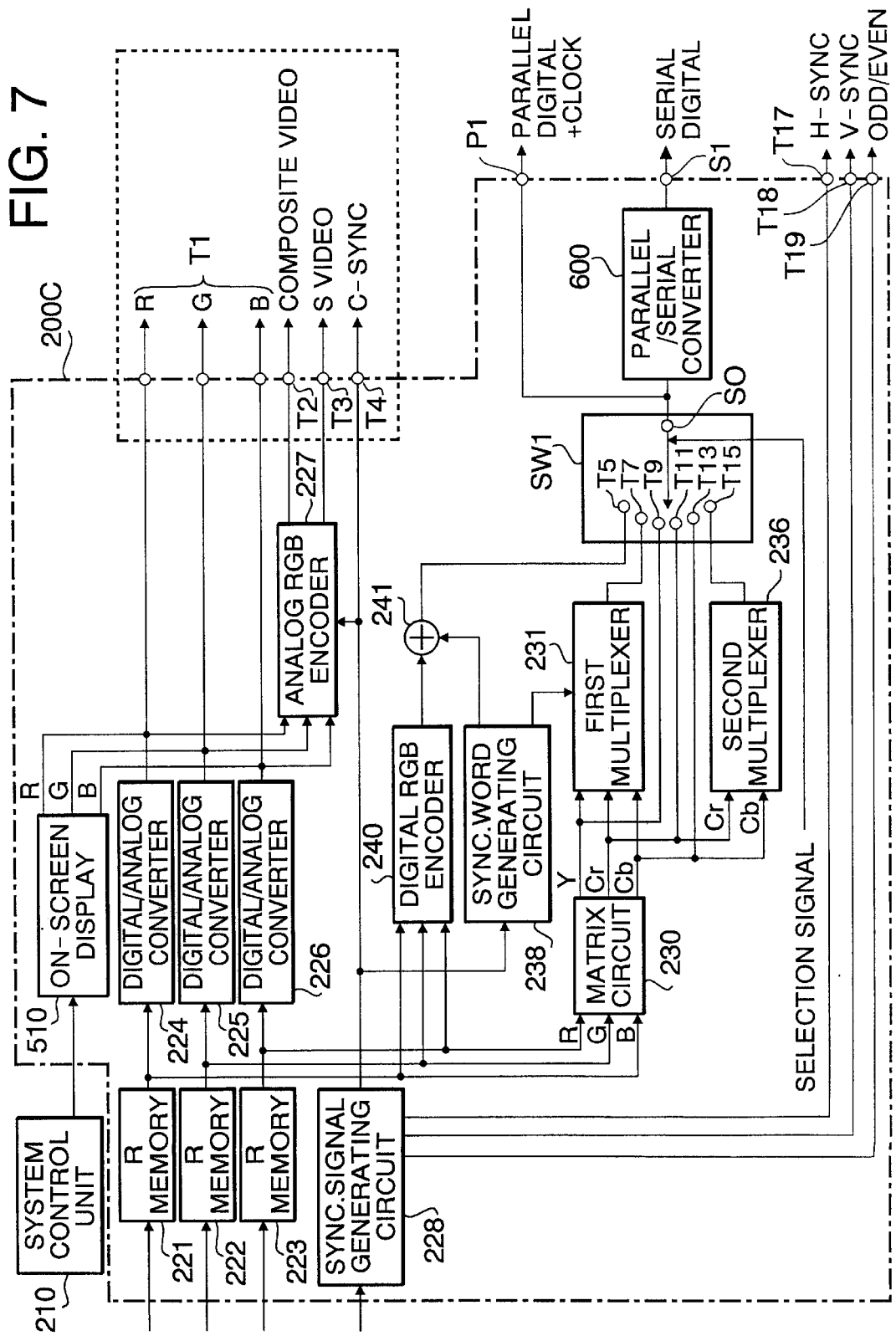
FIG. 7 is a block diagram of a video process unit according to a fourth embodiment of the invention.

FIG. 7 shows a video process unit 220c according to a fourth embodiment of the invention. In the video process unit 220C, the ports T5, T7, T9, T11, T13 and T15 are provided inside a switching device SW1. An output port SO1 of the switching device SW1 is connected to a parallel signal output port P1 directly, and to a serial signal output port S1 by way of a parallel/serial converter 600. The parallel digital signal output through the parallel signal output port P1 includes the parallel digital video signal and a clock signal. The parallel/serial converter 600 is similar to those described in the first embodiment, and a transmission rate of the signal output through the serial signal output port S1 in this embodiment is also 270 Mb/sec.

Switching operation for connecting the output port SO1 with one of the ports T5, T7, T9, T11, T13 and T15 is controlled in accordance with a selection signal output by the system control unit 210. Specifically, when an operator inputs a command indicating a format to be selected through the keyboard 290, the system control unit 210 transmits the selection signal to the switching unit SW1, and one of the ports T5, T7, T9, T11, T13 and T15 is connected to the output port SO1. For example, if the port T5 is selected, the port T5 is connected to the output port SO1. Then, the composite parallel digital video signal in D2 format can be output through the parallel signal output port P1, and the composite serial digital video signal in D2 format can be output through the serial signal output port S1. It should be noted that, if a manually operable member is provided to switch the connection between the output port SO1, and the output ports T5, T7, T9, T11, T13 and T15, it is possible to manually switch the connection without using the system control unit 210.

It should be noted that the ports T5, T7, T9, T11, T13 and T15 are for outputting the parallel signals, and accordingly, each port has a plurality of terminals. In the accompanying drawings, for simplicity, the plurality of terminals are not shown but represented by a port.

Further, in FIG. 7, only one switching unit SW1 and output ports P1 and S1 for outputting the parallel and serial signals selected by the switching unit SW1 are illustrated. In practice, it may be preferable to provide a plurality of switching unit SW2, SW3, . . . , SWn, having the same structure, and corresponding output ports P2, P3, . . . , Pn, S2, S3, . . . , Sn and the same number of parallel/serial converters 600. With such a construction, the operator can select a plurality of signals and use the same individually or in combination.

According to the fourth embodiment, the video process unit 220C is further provided an on-screen display controller 510. The selection signal, which is transmitted to the switching unit SW1, is also transmitted to the on-screen display controller 510. The on-screen display controller 510 generates image signal indicating the selected format for RGB components, and add the output signals of the D/A converters 224 through 226. Thus, the analog RGB signals includes a format information indicating the selected format. The image signals output by the on-screen display controller 510 are also transmitted to the analog RGB encoder 227. Accordingly, the analog composite video signal and S video signal also include the format information.

In the fourth embodiment, the video signals of the same format are output through the ports P1 and S1 as the parallel and serial signals. It may be possible to modify the video process unit to output parallel and serial video signals having different formats through the output ports. Such a modification will be described with reference to FIG. 8.

Figure 8:
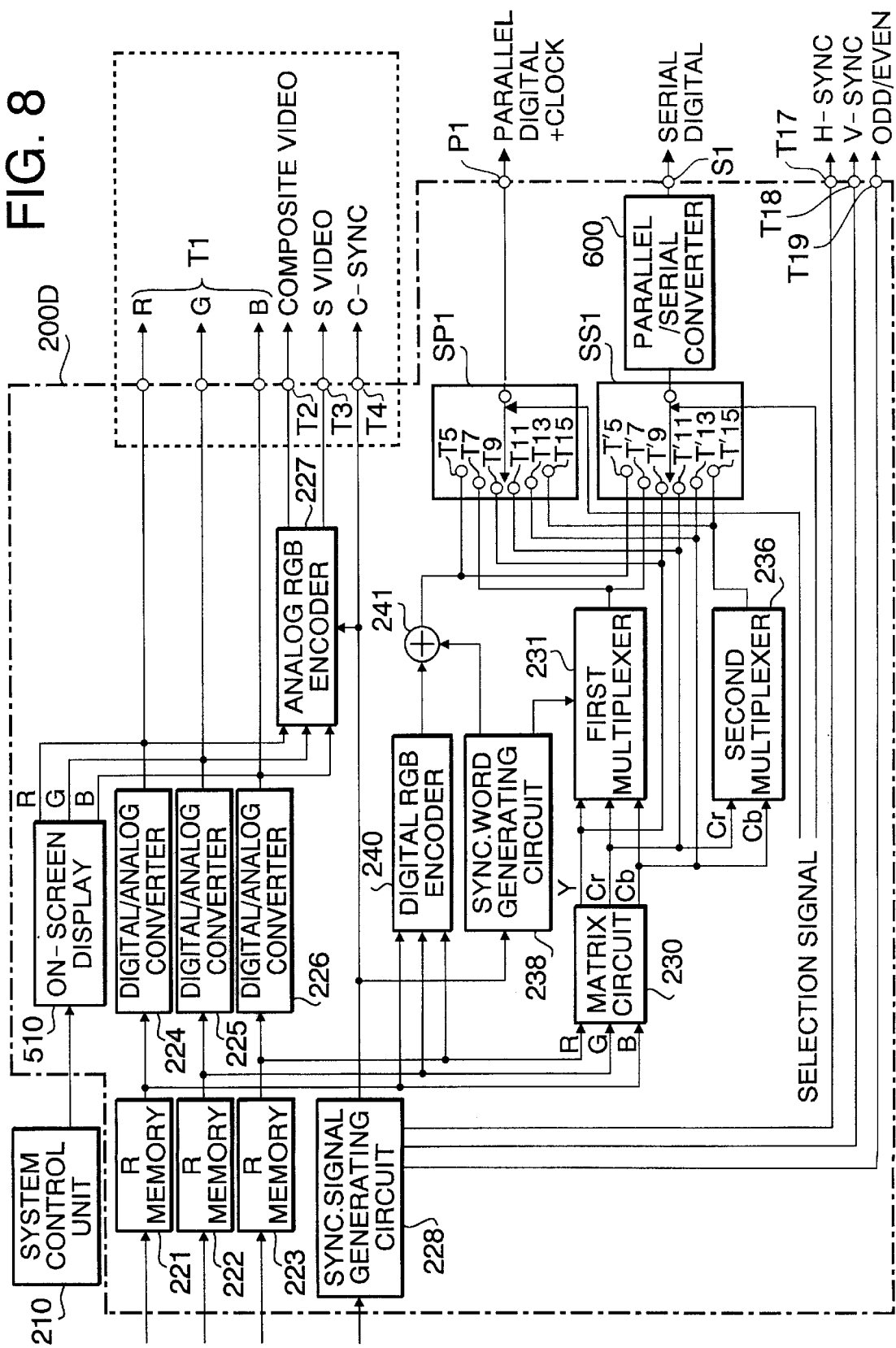
FIG. 8 is a block diagram of a video process unit according to a fifth embodiment of the invention.

FIG. 8 shows a video process unit 220D according to a fifth embodiment of the invention.

The video process unit 220D is provided with a switching unit SP1 for parallel ports, and a switching unit SS1 for serial ports. The switching units SP1 and SS1 are identical to the switching unit SW1 provided in the video process unit 220C. The ports T5, T7, T9, T11, T13 and T15 are provided inside the switching unit SP1, and one of the ports T5, T7, T9, T11, T13 and T15 is connected to the output port SPO which is directly connected to the parallel signal output port P1. Similarly to the fourth embodiment, a parallel video signal and a clock signal is output through the parallel signal output port P1. The switching unit SS1 has the same structure as the switching unit SP1. Ports T'5, T'7, T'9, T'11, T'13 and T'15 are connected in parallel with the ports T5, T7, T9, T11, T13 and T15, respectively. An output port SSO of the switching unit SS1 is connected to the parallel/serial converter 600 which is identical to that employed in the fourth embodiment. The converted signal output from the parallel/serial converter 600 is output through the serial digital signal output port S1.

In the fifth embodiment, the system control unit 210 outputs a first and second selection signals for controlling switching units SP1 and SS1, respectively. Thus, one of the ports T5, T7, T9, T11, T13 and T15 can be connected to the output port SPO of the switching unit SP1, and regardless of the connecting status of the switching unit SP1, any one of the ports T'5, T'7, T'9, T'11, T'13 and T'15 can be connected to the output port SSO of the switching unit SS1.

It should be noted that the switching units SP1 and SS1 need not be the same units, but can be modified to output signals in different formats.

Further, in FIG. 8, only the switching units SP1 and SS1, and output ports P1 and S1 for outputting the parallel and serial signals are illustrated. In practice, it may be preferable to provide a plurality of switching unit SP2, SP3, . . . , SPn, SS2, SS3, . . . having the similar structure, and corresponding output ports P2, P3, . . . , Pn, S2, S3, . . . , Sn and the same number of parallel/serial converters 600. With such a construction, the operator can select a plurality of signals and use the selected signals individually or in combination.

The first to fifth embodiments are described as separate embodiments. However, it may be possible to combine some of the embodiments so that some of the digital signals are output simultaneously through a plurality of output ports, and the other digital signals are selectably output through a single port.

The present disclosure relates to subject matters contained in Japanese Patent Applications No. HEI 09-111919, and No. HEI 09-111920, both filed on Apr. 14, 1997, which are expressly incorporated herein by reference in their entireties.

What is claimed is:

1. An electronic endoscope system, comprising:
   an endoscope unit having a solid-state imaging element which captures an image of an object and outputs an image signal, said endoscope unit being provided with a connection unit;
   an image signal processing device having a body to which said endoscope unit is detachably connected via said connection unit, said image signal processing device including a signal processing unit within said body, said signal processing unit receiving said image signal from said imaging element and generating a plurality of digital video signals having different signal formats, said signal processing unit comprising a plurality of converter circuits that generate said plurality of digital video signals having different signal formats, each converter circuit generating a digital video signal of a different format from every other convertor circuit;
   a plurality of external digital output connectors on said body of said image signal processing device, each external digital output connector outputting one of said plurality of digital video signals having different signal formats, and wherein no digital-to-analog conversion intervenes between said connection unit and said external digital output connectors;
   an analog output system for processing said image signal as a plurality of analog video signals having different analog signal formats; and
   a plurality of external analog output connectors on said body of said image signal processing device, each external analog output connector outputting one of said analog video signals having differing analog signal formats.

2. The electronic endoscope system according to claim 1, wherein said plurality of external digital signal output connectors include at least one serial connector for outputting one of said plurality of digital video signals.

3. The electronic endoscope system according to claim 1, wherein said plurality of external digital signal output connectors include at least one parallel connector for outputting at least one of said plurality of digital video signals.

4. The electronic endoscope system according to claim 1, wherein said plurality of external digital signal output connectors include at least one pair of serial and parallel connectors for outputting at least one of said plurality of digital video signals having different signal formats as serial and parallel digital signals, respectively.

5. The electronic endoscope system according to claim 4, wherein said plurality of external digital signal output connectors include a plurality of pairs of serial and parallel connectors for outputting all of said plurality of digital video signals having different signal formats as serial and parallel digital signals, respectively.

6. The electronic endoscope system according to claim 5, wherein each pair of a parallel connector and a serial connector corresponding to the same signal format are arranged closely adjacent to each other.

7. The electronic endoscope system according to claim 6, wherein each pair of a parallel connector and a serial connector corresponding to the same signal format are arranged closer to one another on said body than to any other pair of a parallel connector and a serial connector.

8. The electronic endoscope system according to claim 7, wherein each pair of a parallel connector and a serial connector corresponding to the same signal format are arranged closer to one another on said body than to any other connector.

9. The electronic endoscope system according to claim 1, wherein said plurality of digital video signals comprises a signal having a D1 format.

10. The electronic endoscope system according to claim 1, wherein said plurality of digital video signals comprises a signal having a D2 format.

11. The electronic endoscope system according to claim 1, wherein said plurality of digital video signals comprises a digital luminance signal.

12. The electronic endoscope system according to claim 1, wherein said plurality of digital video signals comprises digital color difference signals.

13. The electronic endoscope system according to claim 1, wherein said plurality of digital video signals comprises a multiplexed signal which is generated by multiplexing color difference signals.

14. The electronic endoscope system according to claim 1, wherein said plurality of digital video signals comprises a multiplexed signal which is generated by multiplexing brightness and color difference signals.

15. The electronic endoscope system according to claim 1, wherein said signal processing device outputs a field indication signal indicating whether a currently output signal corresponds to an odd or even frame.

16. An electronic endoscope system, comprising:
   an endoscope unit having a solid-state imaging element which captures an image of an object and outputs an image signal, said endoscope unit being provided with a connection unit;
   an image signal processing device having a body to which said endoscope unit is detachably connected via said connection unit, said image signal processing device including a signal processing unit within said body, said signal processing unit receiving said image signal from said imaging element and generating a plurality of digital video signals having different signal formats, said signal processing unit comprising a plurality of converter circuits that generate said plurality of digital video signals having different signal formats, each converter circuit generating a digital video signal of a different format from every other convertor circuit;

an analog output system for processing said image signal as a plurality of analog video signals having different analog signal formats;

a plurality of external analog output connectors on said body of said image signal processing device, each external analog output connector outputting one of said analog video signals having different analog signal formats; and at least one signal selector, which selects one of said plurality of digital video signals having different signal formats; and at least one external digital output connector through which said one of said plurality of digital video signal selected by said signal selector is output, wherein no digital-to-analog conversion intervenes between said connection unit and said at least one external digital output connector.

17. The electronic endoscope system according to claim 16, wherein said at least one external digital output connector comprises a serial connector for outputting a serial digital signal.

18. The electronic endoscope system according to claim 16, wherein said at least one external digital output connector comprises a parallel connector for outputting a parallel digital signal.

19. The electronic endoscope system according to claim 16, wherein said signal processing unit comprises:

a first signal selector, which selects a first signal from among said plurality of digital video signals having different signal formats;

a second signal selector, which selects a second signal from among said plurality of digital video signals having different signal formats;

a parallel output connector through which said first signal is output as a parallel digital signal; and a serial output connector through which said second signal is output as a serial digital signal.

20. An electronic endoscope system, comprising:

an endoscope unit having a solid-state imaging element which captures an image of an object and outputs an image signal, said endoscope unit being provided with a connection unit;

an image signal processing device having a body to which said endoscope unit is detachably connected via said connection unit, said image signal processing device including a signal processing unit within said body, said signal processing unit receiving said image signal from said imaging element and generating a plurality of digital video signals having different signal formats, said signal processing unit comprising:

a frame memory for receiving said image signal on a frame by frame basis and a plurality of converter circuits, each convertor circuit individually connected to said frame memory, that generate said plurality of digital video signals having different signal formats, each converter circuit generating a digital video signal of a different format from every other converter circuit;

a plurality of external digital output connectors on said body of said image processing device, each external digital output connector outputting one of said plurality of digital video signals having different signal formats, and wherein no digital-to-analog conversion intervenes between said connection unit and said external digital output connectors;

an analog output system for processing said image signal as a plurality of analog video signals having different analog signal formats; and a plurality of external analog output connectors on said body of said image signal processing device, each external analog output connector outputting one of said analog video signals having differing analog signal formats.

* * * * *